United States Patent
Salama et al.

(10) Patent No.: US 11,998,533 B2
(45) Date of Patent: Jun. 4, 2024

(54) PHARMACEUTICAL COMPOSITIONS COMPRISING LTV-17 AND BETA-LACTAMASE INHIBITORS AND THEIR USE AS ANTIBACTERIAL AGENTS

(71) Applicant: FEDORA PHARMACEUTICALS INC., Edmonton (CA)

(72) Inventors: Sameeh M. Salama, Edmonton (CA); Samarendra N. Maiti, Edmonton (CA); Renata Jankowska, Edmonton (CA)

(73) Assignee: FEDORA PHARMACEUTICALS INC., Edmonton (CA)

(*) Notice: Subject to any disclaimer, the term of this patent is extended or adjusted under 35 U.S.C. 154(b) by 0 days.

(21) Appl. No.: 17/984,553

(22) Filed: Nov. 10, 2022

(65) Prior Publication Data

US 2023/0149368 A1    May 18, 2023

Related U.S. Application Data

(60) Provisional application No. 63/263,963, filed on Nov. 12, 2021.

(51) Int. Cl.
| | | |
|---|---|---|
| A61K 31/427 | (2006.01) | |
| A61K 31/4188 | (2006.01) | |
| A61P 31/04 | (2006.01) | |

(52) U.S. Cl.
CPC ........ *A61K 31/427* (2013.01); *A61K 31/4188* (2013.01); *A61P 31/04* (2018.01)

(58) Field of Classification Search
CPC .............................. A61K 31/427; A61P 31/04
See application file for complete search history.

(56) References Cited

U.S. PATENT DOCUMENTS

2018/0207142 A1    7/2018 Lamichhane

OTHER PUBLICATIONS

International Search Report and Written Opinion of the International Searching Authority dated Feb. 21, 2023 in International (PCT) Application No. PCT/IB2022/060852.
Starr, Jeremy et al., "Siderophore Receptor-Mediated Uptake of Lacticivin Analogues in Gram-Negative Bacteria", Journal of Medicinal Chemistry, 2014, vol. 57, pp. 3845-3855.
Calvopiña Karina et al., "Sideromimic Modification of Lactivicin Dramatically Increases Potency against Extensively Drug-Resistance *Stenotrophomonas maltophilia* Clinical Isolates", Antimicrobial Agents and Chemotherapy, Jul. 2016, vol. 60, No. 7, pp. 4170-4175.

*Primary Examiner* — Kamal A Saeed
(74) *Attorney, Agent, or Firm* — WENDEROTH, LIND & PONACK, L.L.P.

(57) ABSTRACT

Pharmaceutical combinations of LTV-17 (I), a lactivicin derivative, and β-lactamase inhibitors are provided, wherein the combinations comprise antibacterial agents suitable for use in the treatment or prevention of bacterial infections.

14 Claims, No Drawings

PHARMACEUTICAL COMPOSITIONS COMPRISING LTV-17 AND BETA-LACTAMASE INHIBITORS AND THEIR USE AS ANTIBACTERIAL AGENTS

TECHNICAL FIELD

The present invention is directed to pharmaceutical compounds and their use in the treatment of microbial infections. More particularly, pharmaceutical combinations of a lactivicin derivative having antibacterial activity in combination with certain β-lactamase inhibitors that together are synergistically active against a number of resistant pathogenic microorganisms are provided.

BACKGROUND ART

While resistant bacterial isolates continue to emerge in the hospital setting, physicians are also encountering an increasing number of resistant bacteria in the community, particularly the multi-drug resistant Gram (−) pathogens including the bacteria that constitute the ESKAPE pathogens (*Enterococcus faecium, Staphylococcus aureus, Klebsiella pneumoniae, Acinetobacter baumannii, Pseudomonas aeruginosa* and *Enterobacter* species). One of the most common resistance mechanisms to commonly used β-lactam antibiotics is the production, by resistant bacteria, of a group of enzymes called β-lactamases. To overcome this resistance, β-lactamase inhibitors have been developed by many groups and they are commonly used in clinical settings.

Another option is to develop new classes of antibacterial agents. Given the rise in the expression of bacterial β-lactamases, effective agents may be those having a non-β-lactam structural motif.

The development of synergistic combinations of antibacterial agents and β-lactamase initiators would also augment the current arsenal of available antimicrobial therapies.

The present invention is directed to the development of such new antibacterial treatments and other important goals.

SUMMARY OF THE INVENTION

In view of the increasing resistance development by ESKAPE pathogens against commonly used β-lactam antibiotics, there is an ongoing need to find suitable antibacterial agents for use in the treatment of bacterial infections, such as agents with a non-β-lactam structural motif.

LTV-17 (Formula I; (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid) was developed as a lactivicin derivative lacking a β-lactam structural motif (J. Med. Chem. 2014, 57, 3845-3855).

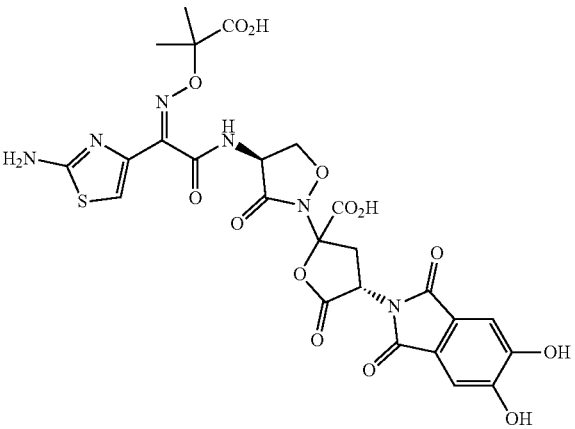

(I)

While LTV-17 (I) shows enhanced antibacterial activity (J. Med. Chem. 2014, 57, 3845-3855), it shows reduced activity against many β-lactamase producing strains and may contribute to significant treatment failure in the clinic. This is due to the fact that while lactivicins are non-β-lactam antibiotics, they are also susceptible to some beta-lactamase enzymes.

However, and as detailed below, it was discovered that when LTV-17 (I) is paired with selected β-lactamase inhibitors, there is a surprising synergistic effect on susceptible bacteria.

The present invention is based on this discovery and it relates to the following embodiments: (i) pharmaceutical combinations and medicaments comprising LTV-17 (I) and one or more β-lactamase inhibitors, (ii) the use of such pharmaceutical combinations and medicaments in the treatment of bacterial infections, and (iii) methods of treating bacterial infections which comprise administering LTV-17 (I) with one or more β-lactamase inhibitors. In each of these embodiments, the β-lactamase inhibitors may be, but are not limited to, compounds selected from the formula ($II^a$) to ($II^c$). Such combinations of LTV-17 (I) and β-lactamase inhibitors exhibit a synergistic effect when used in the treatment of bacterial infections.

In particular, and in a first embodiment, the invention is directed to a pharmaceutical combination comprising compound LTV-17 (I) or a pharmaceutically acceptable salt thereof, solvate thereof, or solvate of the salt thereof:

(I)

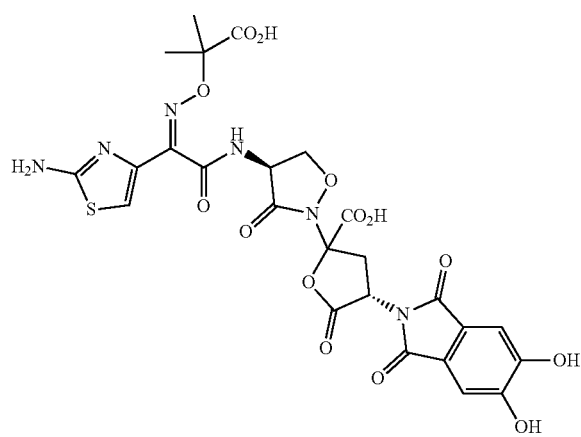

and one or more β-lactamase inhibitor or a pharmaceutically acceptable salt thereof or a biologically hydrolysable prodrug thereof.

In aspects of this embodiment, the one or more β-lactamase inhibitors may be, but are not limited to, compounds selected from the group consisting of compounds (II$^a$) to (II$^{z'}$):

(II$^a$)

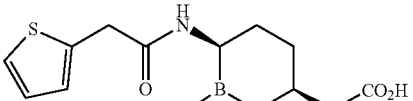

(II$^b$)

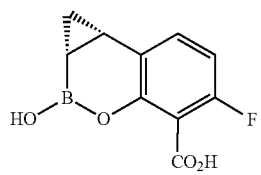

(II$^c$)

(II$^d$)

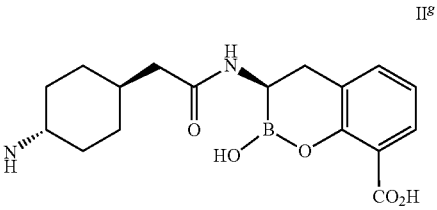

(II$^e$)

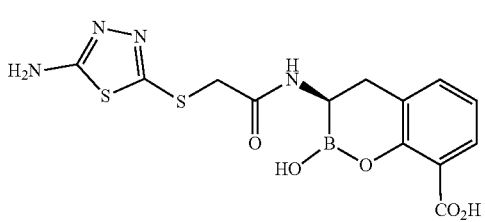

(II$^f$)

(II$^g$)

(II$^h$)

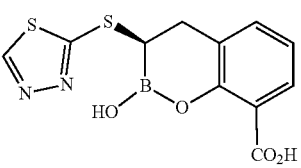

(II$^i$)

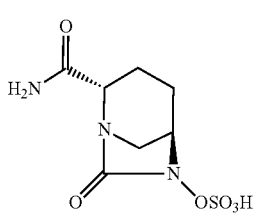

(II$^j$)

(II$^k$)

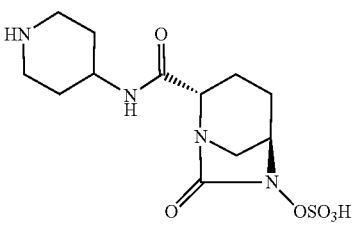

(II$^l$)

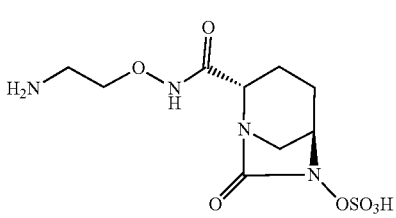

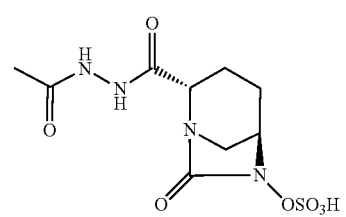
II<sup>m</sup>
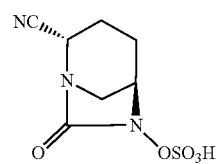
II<sup>n</sup>
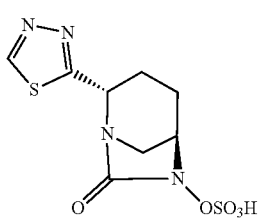
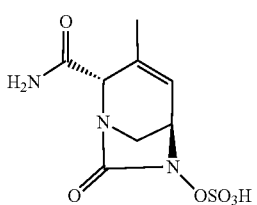
II<sup>p</sup>
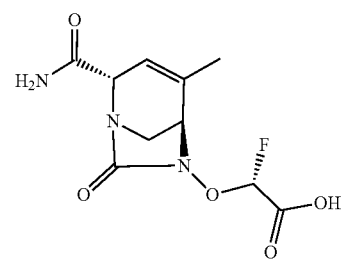
II<sup>q</sup>
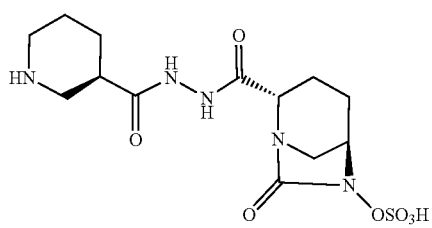
II<sup>r</sup>
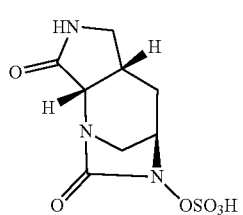
II<sup>s</sup>
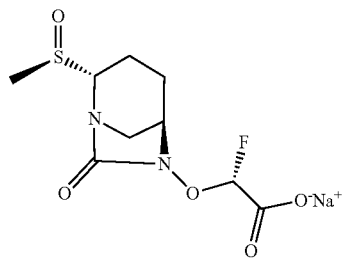
II<sup>t</sup>
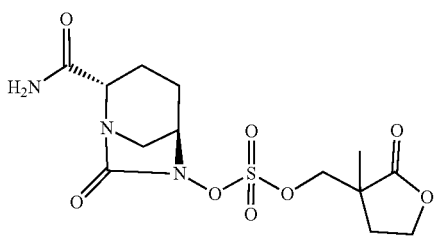
II<sup>u</sup>
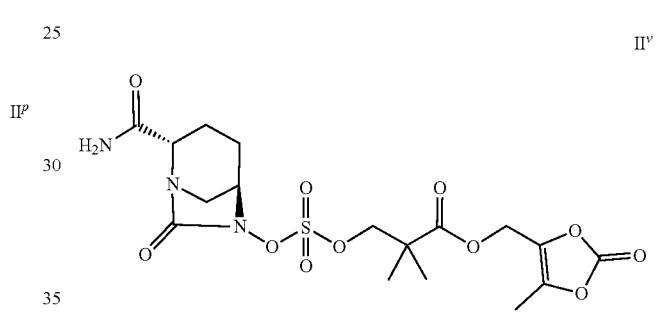
II<sup>v</sup>
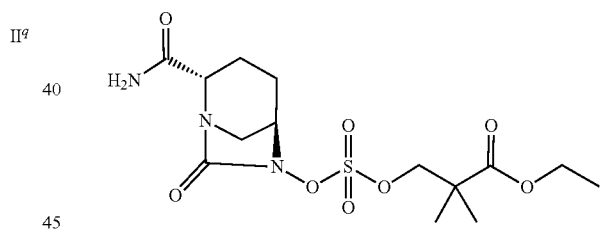
II<sup>w</sup>
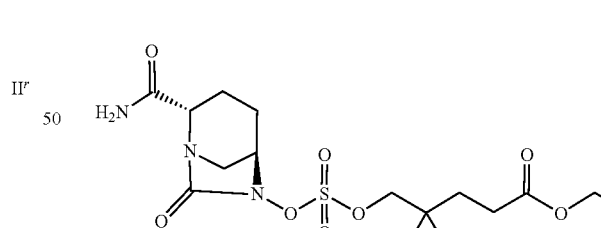
II<sup>x</sup>
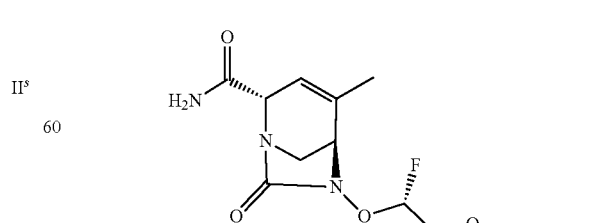
II<sup>y</sup>
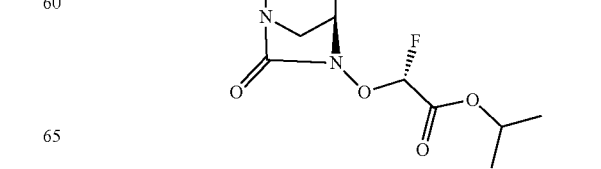

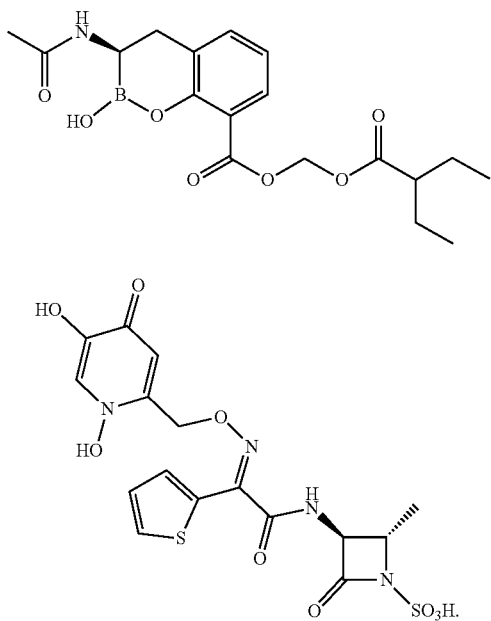

These pharmaceutical combinations of the invention may be used in treating and/or preventing diseases, in particular bacterial infections, especially Gram-negative bacterial infections in humans and in veterinary medicine. They may also be used as medicaments for treating and/or preventing bacterial infections in humans and in veterinary medicine.

In preferred aspects of the invention, the pharmaceutical combinations are synergistic combinations. Thus, the antibacterial activity exhibited by the combination is greater than the sum of the antibacterial activity separately exhibit by (i) LTV-17 (I) and (ii) the one or more β-lactamase inhibitors present in the combination.

The pharmaceutical combinations of the invention will typically comprise a ratio of LTV-17 (I) to β-lactamase inhibitor in a range of 20:1 to 1:20, by weight. In certain aspects, the ratio is in the range of 1:1 to 1:20.

The pharmaceutical combinations of the invention may also comprise a pharmaceutically acceptable diluent, excipient or carrier.

In a second, embodiment, the invention is directed to methods of treating or preventing a bacterial infection in a subject. Such methods comprise administering a therapeutically effective amount of the pharmaceutical combinations of the invention to a subject in need thereof. Such subjects include those having a bacterial infection and those at risk of developing a bacterial infection.

Thus, in one aspect of this embodiment, the invention is directed to a method of treating or preventing a bacterial infection in a subject, comprising administering a therapeutically effective amount of pharmaceutical combination comprising compound LTV-17 (I) or a pharmaceutically acceptable salt thereof, solvate thereof, or solvate of the salt thereof and one or more β-lactamase inhibitor or a pharmaceutically acceptable salt thereof or a biologically hydrolysable prodrug thereof, to a subject having a bacterial infection.

In aspects of this embodiment, the one or more β-lactamase inhibitors may be, but are not limited to, compounds selected from the group consisting of compounds (II$^a$) to (II$^{z'}$) as defined herein.

In certain aspects of the embodiment, the bacterial infection is caused by Gram-negative bacteria.

In preferred aspects of the invention, the pharmaceutical combinations used in the methods of the invention are synergistic combinations. Thus, the antibacterial activity exhibited by the combination is greater than the sum of the antibacterial activity separately exhibit by (i) LTV-17 (I) and (ii) the one or more β-lactamase inhibitors present in the combination.

The pharmaceutical combinations used in the methods of the invention will typically comprise a ratio of LTV-17 (I) to β-lactamase inhibitor in a range of 20:1 to 1:20, by weight. In certain aspects, the ratio is in the range of 1:1 to 1:20.

The pharmaceutical combinations used in the methods of the invention may also comprise a pharmaceutically acceptable diluent, excipient or carrier.

The subject subjected to treatment may be any subject in which the pharmaceutical combinations of the invention will have a therapeutic effect, such as a human.

DETAILED DESCRIPTION OF THE INVENTION

The Lactivicin class of antimicrobial agents are active against a range of Gram-positive and Gram-negative bacteria. These compounds have a unique dicyclic peptide core that exhibits excellent antibacterial activity, particularly against Gram (−) microorganisms. Natural lactivicin, a non-β-lactam antibiotic which is 2-[(4S)-4-acetamido-3-oxo-1,2-oxazolidin-2-yl]-5-oxooxolane-2-carboxylic acid, showed improved antibacterial activity when the acylamino moiety at C-4 position was modified and replaced with 2-aminothiazol-4-yl-(Z)-2-methoxy-iminoacetyl sidechain.

LTV-17 (Formula I; (4S)-2-[(4S)-4-{[(2Z)-2-(2-amino-1,3-thiazol-4-yl)-2-{[(2-carboxypropan-2-yl)oxy]imino}acetyl]amino}-3-oxo-1,2-oxazolidin-2-yl]-4-(5,6-dihydroxy-1,3-dioxo-1,3-dihydro-2H-isoindol-2-yl)-5-oxooxolane-2-carboxylic acid), is one such lactivicin derivative bearing a catechol moiety in the molecule that utilizes a broad set of Ton-B-dependent iron transport mechanisms and therefore enhances siderophore receptor mediated uptake across the bacterial outer membrane. The present invention relates to combinations of LTV-17 (I) with various β-lactamase inhibitors that show synergistic activity against a number of antibiotic-resistant bacteria.

Pharmaceutical Combinations

As summarized above, the invention is directed to pharmaceutical combinations comprising compound LTV-17 (I) or a pharmaceutically acceptable salt thereof, solvate thereof, or solvate of the salt thereof and one or more β-lactamase inhibitor or a pharmaceutically acceptable salt thereof or a biologically hydrolysable prodrug thereof. In aspects of the invention, the one or more β-lactamase inhibitors may be, but are not limited to, compounds selected from the group consisting of compounds (II$^a$) to (II$^{z'}$) as set forth herein.

These pharmaceutical combinations of the invention may be used in treating and/or preventing diseases, in particular bacterial infections, especially Gram-negative bacterial infections in humans and in veterinary medicine. They may also be used as medicaments for treating and/or preventing bacterial infections in humans and in veterinary medicine.

Methods

As further summarized above, the invention is also directed to methods of treating or preventing a bacterial infection in a subject. Such methods comprise administering a therapeutically effective amount of the pharmaceutical combinations of the invention to a subject in need thereof. Such subjects include those having a bacterial infection and those at risk of developing a bacterial infection.

As a non-limiting example, the invention is directed to a method of treating or preventing a bacterial infection in a subject, comprising administering a therapeutically effective amount of pharmaceutical combination comprising compound LTV-17 (I) or a pharmaceutically acceptable salt thereof, solvate thereof, or solvate of the salt thereof. In aspects of the invention, the one or more β-lactamase inhibitors may be, but are not limited to, compounds selected from the group consisting of compounds $(II^a)$ to $(II^{z'})$ as set forth herein.

As used in each of the embodiments and aspects of the invention, the term "β-lactamase inhibitor" refers to a compound which is capable of inhibiting β-lactamase activity, where inhibiting activity means inhibiting the activity of a class A, B, C and/or D β-lactamases by at least 50%, 60%, 70%, 80%, 90%, 95% or more. Suitable β-lactamase inhibitors for use in the combinations and methods of the invention include compounds $(II^a)$ to $(II^{z'})$ as set forth herein.

As used in each of the embodiments and aspects of the invention, the term "β-lactamase" denotes an enzyme capable of inactivating a β-lactam antibiotic.

The present invention further relates to the use of the "pharmaceutical combinations" invention, i.e. those comprising of LTV-17 (I) and one or more of the β-lactamase inhibitors, such as the compounds of the formula $(II^a)$ to $(II^{z'})$ or a pharmaceutically acceptable salt thereof or a biologically hydrolysable prodrug as mentioned above, for the production of medicaments that may be used in the treatment and/or prophylaxis of diseases, especially of bacterial infections.

The present invention further relates to medicaments which comprise LTV-17 (I), or a pharmaceutically acceptable carriers or diluents and one or more β-lactamase inhibitors or a pharmaceutically acceptable salt thereof or a biologically hydrolysable prodrug selected from any of the formula $(II^a)$ to $(II^{z'})$ as mentioned above.

The "pharmaceutical combinations" of this invention are particularly useful in humans and veterinary medicine for the prophylaxis and treatment of local and systemic infections.

The "pharmaceutical combinations" of this invention means the physical combination of LTV-17 (I) and one or more β-lactamase inhibitors as cited above in a suitable ratio.

In a pharmaceutical composition or medicament containing the "pharmaceutical combinations" of LTV-17 (I) and one or more of the β-lactamase inhibitors, the weight ratio of active ingredient to carrier will normally be in the range of 1:20 to 20:1. In certain aspects, the ratio is in the range of 1:1 to 1:20.

The "pharmaceutical combinations" of this invention include salts, solvates and solvates of the salts thereof of the LTV-17 (I) in the combination.

The "pharmaceutical combinations" of this invention may contain a compound containing enantiomers or diastereomers and respective mixtures thereof.

The "pharmaceutical combinations" of this invention may contain a compound containing a tautomeric form, so the present invention encompasses all tautomeric forms.

When co-administered with a β-lactamase inhibitor, LTV-17 (I) provides a synergistic effect. The term "synergistic effect" refers to the effect produced when two or more agents are co-administered that is greater than the effect produced when the agents are administered individually.

While LTV-17 (I) and the one or more β-lactamase inhibitors may be co-administered to a subject, either in the sample pharmaceutical formulation or in separate pharmaceutical formulations but administered concurrently, and thus form the basis of the "pharmaceutical combinations" of the invention, it should be understood that LTV-17 (I) or a pharmaceutically acceptable salt thereof can be administered as a separate agent during a course of treatment with the β-lactamase inhibitor or a pharmaceutically acceptable salt thereof or a biologically hydrolysable prodrug also being administered separately. Thus, LTV-17 (I) and the one or more β-lactamase inhibitors can be administered sequentially or concurrently, in any order, with overlapping or non-overlapping periods of administration. A synergistic effect can be achieved even when these agents are administered sequentially with non-overlapping periods of administration if the agents are administered in close temporal proximity, e.g. with the two agents administered within one hour or so of each other.

"Therapeutically effective amount" refers to the amount of the pharmaceutical combination, when administered to a subject for treating a disease, sufficient to affect such treatment of the disease, disorder or symptom. The therapeutically effective amount can vary depending, for example, on the "pharmaceutical combination", the disease, disorder, and/or symptoms of the disease, severity of the disease, disorder, the age, weight, and/or health of the patient to be treated.

Typically, the therapeutically effective amount of a pharmaceutical combination of the invention for adult humans is about 50 mg to about 3000 mg of the active agents. In another embodiment, the therapeutically effective amount is about 100 mg to about 2000 mg. In another embodiment, the therapeutically effective amount is about 500 mg to about 1200 mg. Typically, the dosages (noted amounts) are given 1 to 4 times per day. In one embodiment, the dosages are given 3 times per day. In some cases, it may be necessary to use dosages outside these limits.

The terms "dose", "unit dose", "unit dosage" or "effective dose" refers to physically discrete units that contain a predetermined quantity of active ingredient calculated to produce a desired therapeutic effect.

The present invention further relates to medicaments which comprise a pharmaceutical combination of the invention, usually together with one or more inert, non-toxic, pharmaceutically acceptable carrier or diluent, as well as to their use for the aforementioned purposes. The compositions can take the form of injectable preparations, suspensions, emulsions, coated tablets, pellets, gelatin-capsules, capsules containing liquids, powders, granules, sustained release formulations, suppositories, aerosols, sprays, ointments, creams or any other form suitable for use.

The "pharmaceutical combinations" may act systemically or locally. They can for this purpose be administered in a suitable way such as, for example, parentally, pulmonarily, nasally, sublingually, lingually, buccally, rectally, dermally, transdermally, conjunctivally, otically or as an implant or stent.

For these administration routes the "pharmaceutical combinations" of the present invention can be administered in suitable administration forms. Thus, the pharmaceutical combinations of the invention may also comprise a pharmaceutically acceptable diluent, excipient or carrier.

Parenteral administration can take place with avoidance of an absorption step (e.g. intravenous, intraarterial, intracardiac, intraspinal or intralumbar) or with inclusion of an absorption step (e.g. intramuscular, subcutaneous, intracutaneous, percutaneous or intraperitoneal). Administration forms suitable for parenteral administration are, inter alia, preparations for injection and infusion in the form of solutions, suspensions, emulsions, lyophilizates or sterile powders.

Suitable for the other administration routes are, for example, pharmaceutical forms for inhalation (inter alia powder inhalers, nebulizers), nasal drops, solutions, sprays, tablets, films/wafers or capsules, for lingual, sublingual or buccal administration, suppositories, preparations for ears or eyes, aqueous suspensions (lotions, shaking mixtures), lipophilic suspensions, ointments, creams, transdermal therapeutic systems (such as for example patches), pastes, foams, dusting powders, implants or stents.

The pharmaceutical combinations of the invention can be converted into the stated administration forms, i.e. the pharmaceutical compositions of the invention. This can take place in a manner known per se by mixing with inert, non-toxic, pharmaceutically acceptable carriers or diluents such as starch, glucose, lactose, sucrose, gelatin, gum Arabic, malt, rice, flour, chalk, silica gel, sodium stearate, glycerol monostearate, talc, sodium chloride, dried skim milk, glycerol, propylene glycol, water, water-for-injection, saline, buffered saline, dextrose, glycerol, ethanol, propylene glycol, polysorbate 80 (Tween-80™), poly(ethylene) glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, liposomes, vesicles, particles, and liposomes. The terms specifically exclude cell culture medium.

Pharmaceutical compositions of the present invention, if desired, can also contain minor amounts of wetting agents (for example sodium dodecyl sulfate, polyoxyethylene sorbitan oleate), dispersing or emulsifying agents, or pH buffering agents, and preservatives. In addition, auxiliary, stabilizing, thickening, lubricating, and coloring agents can be included. Pharmaceutical compositions can be formulated in a conventional manner. Proper formulation is dependent upon the route of administration chosen.

In pharmaceutical compositions comprising the pharmaceutical combinations of the invention, the weight ratio of active ingredient to carrier will normally be in the range of 1:20 to 20:1.

Examples of bacteria against which the compounds of the invention will have antibacterial activity include, but are not limited to, one or more of Enterobacterales, *Escherichia coli, Enterobacter* spp., *Klebsiella* spp., *Serratia* spp., *Pseudomonas* spp., *Stenotrophomonas* spp., *Citrobacter* spp., *Acinetobacter* spp., *Campylobacter* spp., *Helicobacter* spp., *Vibrio* spp., *Bordetella* spp., *Salmonella* spp., *Shigella* spp., *Francisella* spp., *Burkholderia* spp., *Clostridia* spp., *Alcaligenes* spp., *Moraxella* spp., *Proteus* spp., *Neisseria* spp., *Haemophilus* spp., *Achromobacter* spp. and *Erwinia* spp. Specific genera of bacteria against which the compounds of the invention will have antibacterial activity include, but are not limited to, one or more of the ESKAPE pathogens, i.e. *Enterococcus faecium, Staphylococcus aureus, Klebsiella pneumoniae, Acinetobacter baumannii, Pseudomonas aeruginosa* and *Enterobacter* species.

Animals of veterinary medicine that may be treated using the pharmaceutical combinations and methods of the invention include, but are not limited to, a non-human primate, bird, horse, cow, goat, sheep, a companion animal, such as a dog, cat or rodent, or other mammal.

EXAMPLES

Synergistic activities of the pharmaceutical combinations, without limiting to specific combinations, are provided in Table 1.

TABLE 1

Synergistic activity of LTV-17 (I) in combination with β-lactamase inhibitor (II') Avibactam: MIC of LTV-17 (I) with and without Avibactam (II') in µg/ml

| Collection Number | Organism | AmpC | MIC of LTV-17 (µg/ml) | MIC of LTV-17 Plus Avibactam (µg/ml) | Number of two-fold dilution decrease in MIC |
|---|---|---|---|---|---|
| 552115 | Enterobacter cloacae species complex | Elevated AmpC | 2 | 0.12 | 4 |
| 827002 | Escherichia coli | Elevated AmpC | 0.03 | ≤0.008 | ≥2 |
| 841741 | Escherichia coli | Elevated AmpC | 0.25 | ≤0.008 | ≥5 |
| 850348 | Escherichia coli | Elevated AmpC | 1 | 0.015 | 6 |
| 850361 | Escherichia coli | Elevated AmpC | 0.06 | ≤0.008 | ≥3 |
| 1043714 | Escherichia coli | Elevated AmpC | 0.06 | ≤0.008 | ≥3 |
| 1047951 | Escherichia coli | Elevated AmpC | 0.12 | 0.03 | 2 |
| 1056585 | Citrobacter freundii species complex | Elevated AmpC | 0.5 | 0.03 | 4 |
| 1057610 | Enterobacter cloacae species complex | Elevated AmpC | 0.25 | ≤0.008 | ≥5 |
| 1083996 | Enterobacter cloacae species complex | Elevated AmpC | 0.5 | 0.06 | 3 |
| 1152443 | Escherichia coli | CMY-DHA | 0.5 | 0.03 | 4 |
| 1160670 | Escherichia coli | CMY-DHA | 0.12 | ≤0.008 | ≥4 |
| 1165490 | Escherichia coli | CMY-DHA | 0.5 | ≤0.008 | ≥6 |
| 1165546 | Escherichia coli | CMY-DHA | 0.5 | 0.06 | 3 |
| 1167103 | Escherichia coli | CMY-DHA | 0.5 | ≤0.008 | ≥6 |
| 1167174 | Escherichia coli | CMY-DHA | 4 | 0.12 | 5 |
| 1167846 | Klebsiella pneumoniae | CMY-DHA | 1 | 0.25 | 2 |
| 1165173 | Escherichia coli | CMY-DHA | 0.25 | ≤0.008 | ≥5 |
| 1160345 | Escherichia coli | CMY-DHA | 0.5 | ≤0.008 | ≥6 |
| 1159308 | Proteus mirabilis | CMY-DHA | 4 | ≤0.008 | ≥9 |

Method for In Vitro Antibacterial Evaluation

Bacterial isolates: Representative resistant strains of *Escherichia coli, Citrobacter freundii, Enterobacter cloacae, Klebsiella pneumoniae*, and *Proteus mirabilis* harboring class-C β-lactamase producers were used to test for the synergistic effect of adding a β-lactamase inhibitor (II') to the antibiotic LTV-17 (I) (Table 1).

Minimum inhibitory concentration (MIC) test procedure: All antibiotics were tested by both the broth microdilution methods according to the Clinical and Laboratory Standards Institute (CLSI) recommendations (M07), and a modified CLSI method that included iron-depleted CA-MHB protocol. The MIC was defined as the lowest concentration of the antibiotic to produce clear wells in the 96-well plates. MIC interpretations were based on the CLSI M100-S23 (2013) and European Committee on Antimicrobial Susceptibility Testing (EUCAST; 2013) breakpoint criteria. Synergistic activity was calculated based on the number of two-fold dilution reduction of the MIC using LTV-17 (I) plus β-lactamase inhibitor Avibactam (II$^j$) compared to MIC of LTV-17 (I) tested alone against the same strains. The higher the number of two-fold reduction, the stronger the synergy is.

Testing Results

LTV-17 (I) and Avibactam (II$^j$) exhibited synergistic activity against the tested strains with a range of two-fold reduction in MIC from 2 to more than 9 fold. Avibactam was tested at a fixed concentration of 4 µg/mL. This data suggests that the addition of a β-lactamase inhibitor to LTV-17 (I) had a significant impact on reducing the concentration of LTV-17 (I)) required to inhibit bacterial growth. This also suggests that the combination product can be used as a therapeutic prophylactic agent or to treat infections caused by resistant strains of Gram-negative bacteria.

We claim:

1. A synergistic pharmaceutical combination comprising compound LTV-17 (I) or a pharmaceutically acceptable salt thereof, solvate thereof, or solvate of the salt thereof:

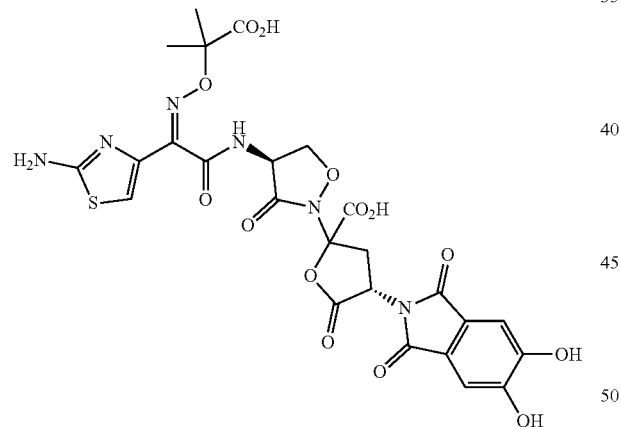

(I)

and one or more β-lactamase inhibitor or a pharmaceutically acceptable salt thereof or a biologically hydrolysable prodrug thereof.

2. The synergistic pharmaceutical combination of claim 1, wherein the one or more β-lactamase inhibitor is selected from the group consisting of compounds (II$^a$) to (II$^z$):

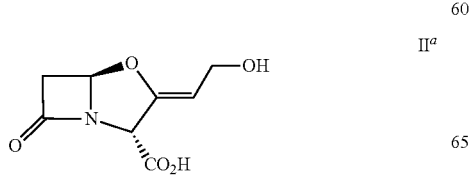

II$^a$

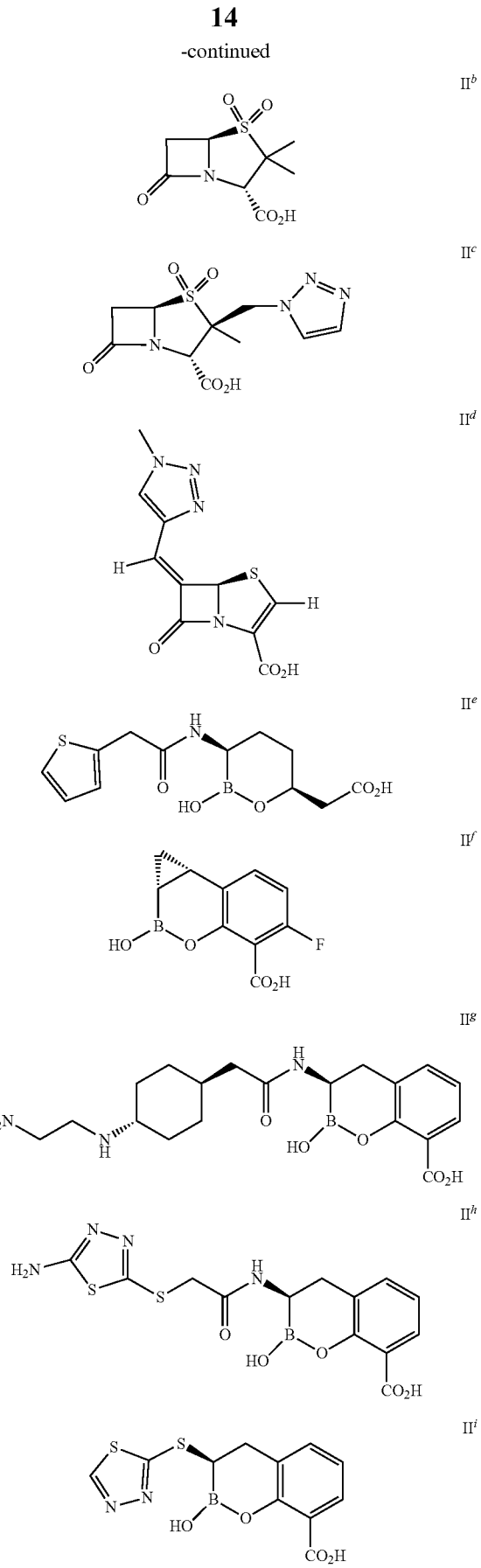

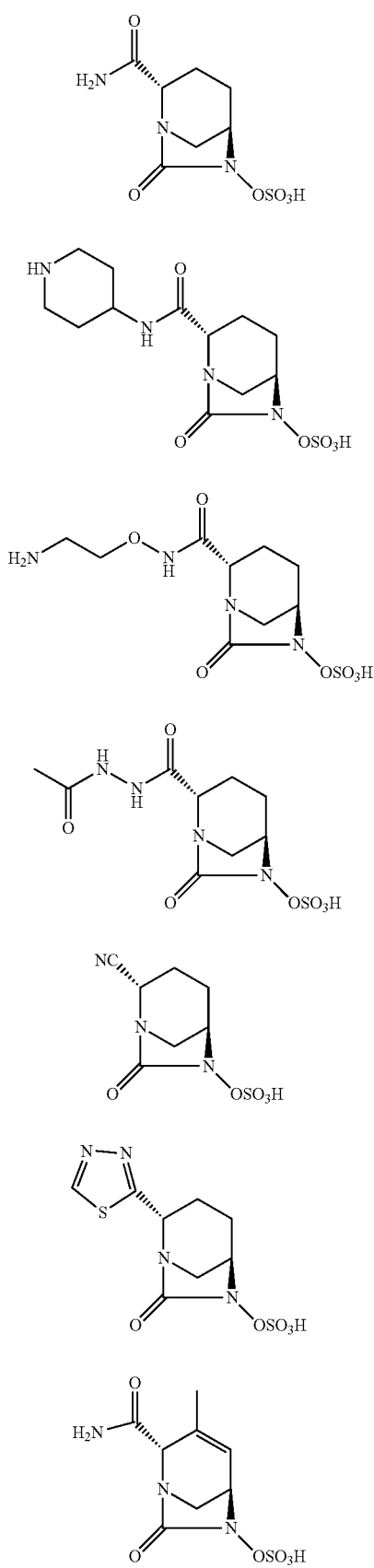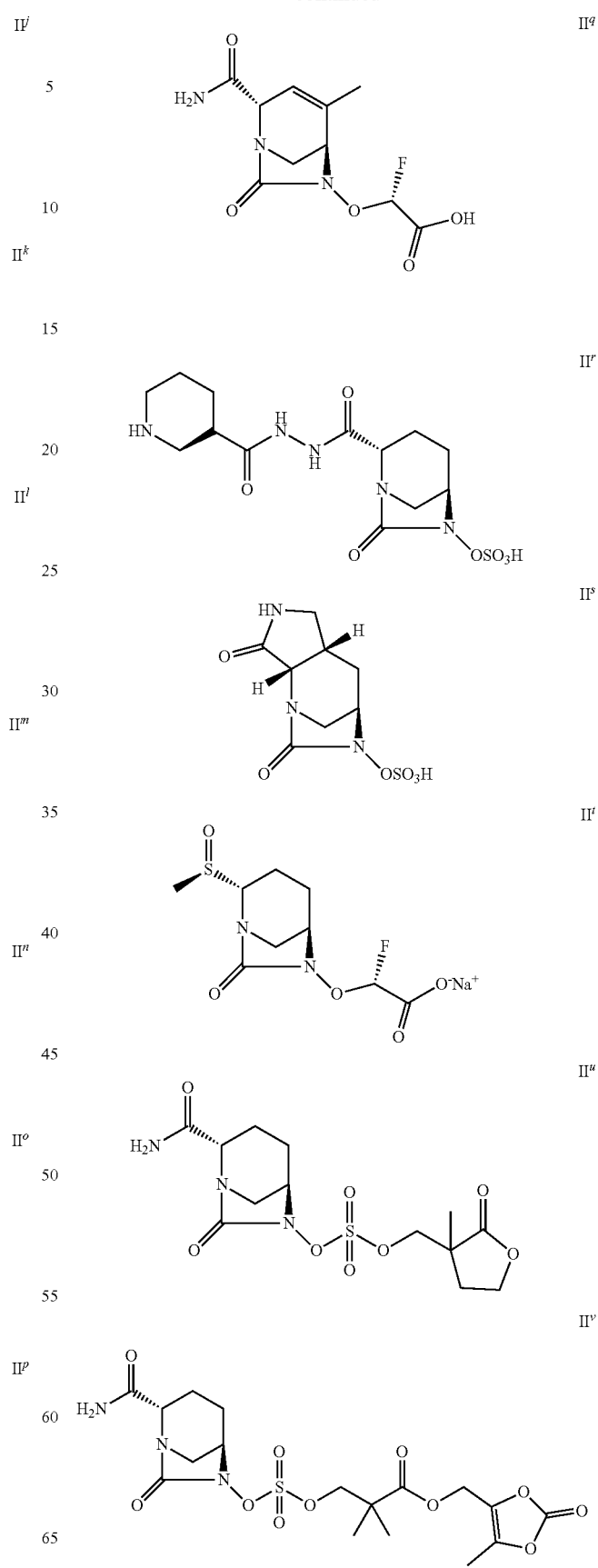

3. The synergistic pharmaceutical combination of claim 1 for use in treating and/or preventing diseases, in particular bacterial infections, especially Gram-negative bacterial infections.

4. The synergistic pharmaceutical combination of claim 1, wherein the combination comprises a ratio of LTV-17 (I) to β-lactamase inhibitor in a range of 20:1 to 1:20, by weight.

5. The synergistic pharmaceutical combination of claim 4, wherein ratio is in the range of 1:1 to 1:20.

6. The synergistic pharmaceutical combination of claim 1, for use as a medicament for treating and/or preventing bacterial infections in humans and in veterinary medicine.

7. The synergistic pharmaceutical combination of claim 1, further comprising a pharmaceutically acceptable diluent, excipient or carrier.

8. A method of treating or preventing a bacterial infection in a subject, comprising administering a therapeutically effective amount of pharmaceutical combination comprising compound LTV-17 (I) or a pharmaceutically acceptable salt thereof, solvate thereof, or solvate of the salt thereof:

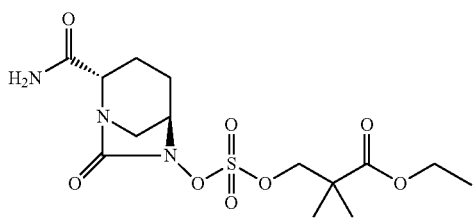

(I)

and one or more β-lactamase inhibitor or a pharmaceutically acceptable salt thereof or a biologically hydrolysable prodrug thereof, to a subject having a bacterial infection, wherein the combination has a synergistic anti-bacterial effect.

9. The method of claim 8, wherein the one or more β-lactamase inhibitor is selected from the group consisting of compounds (IIa) to (IIz'):

-continued
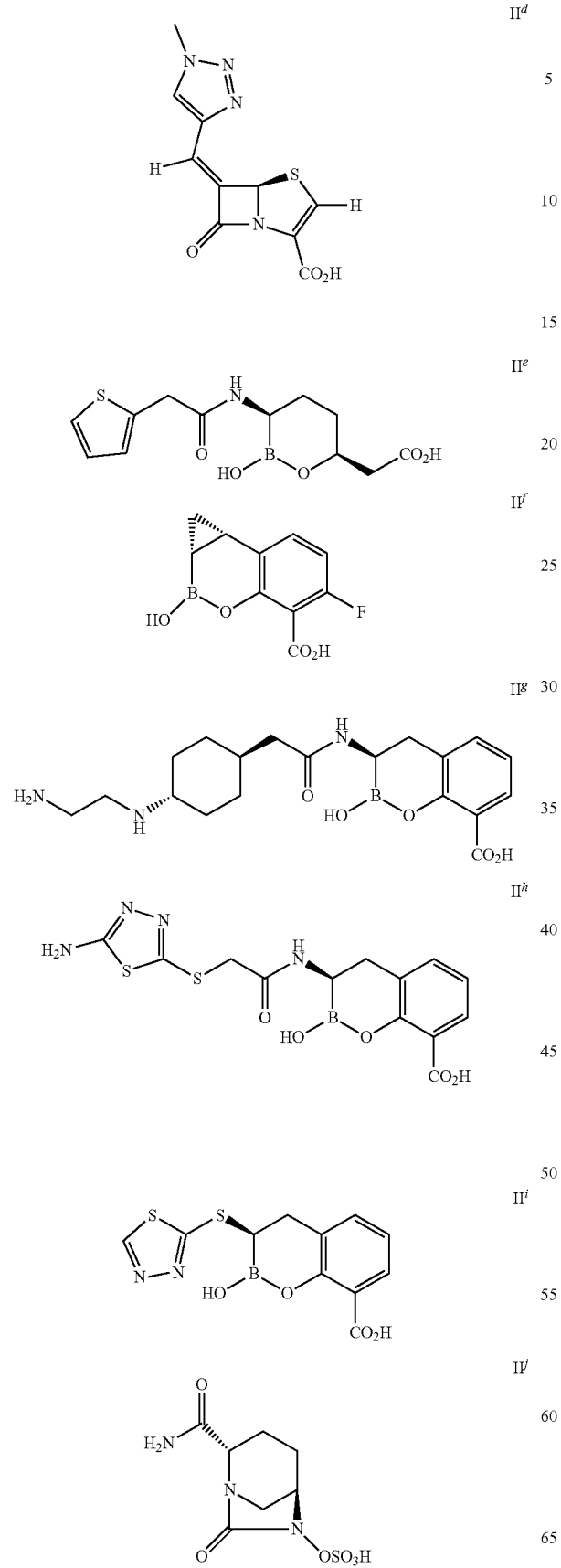
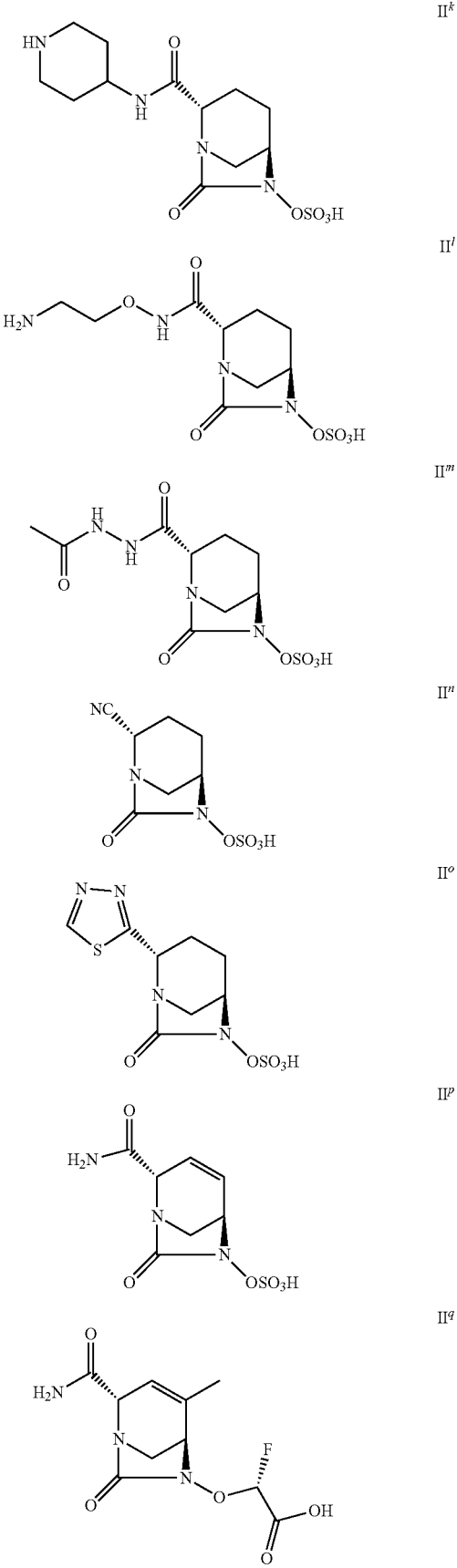

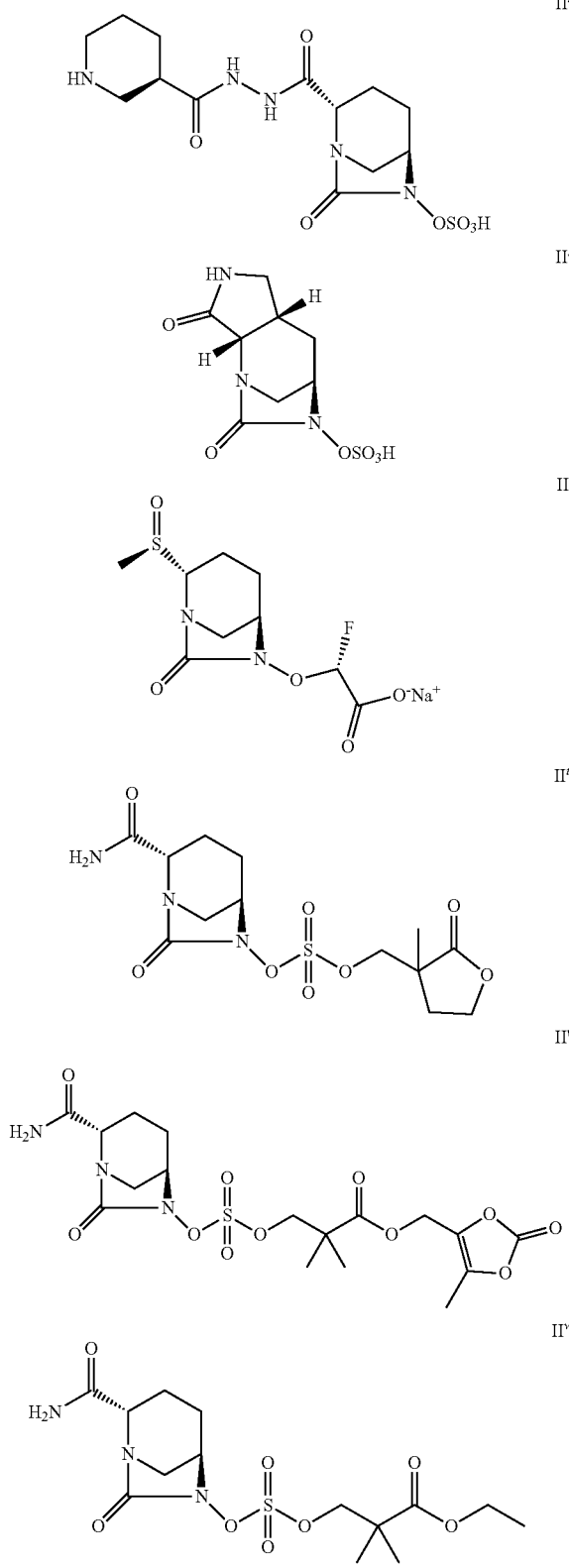
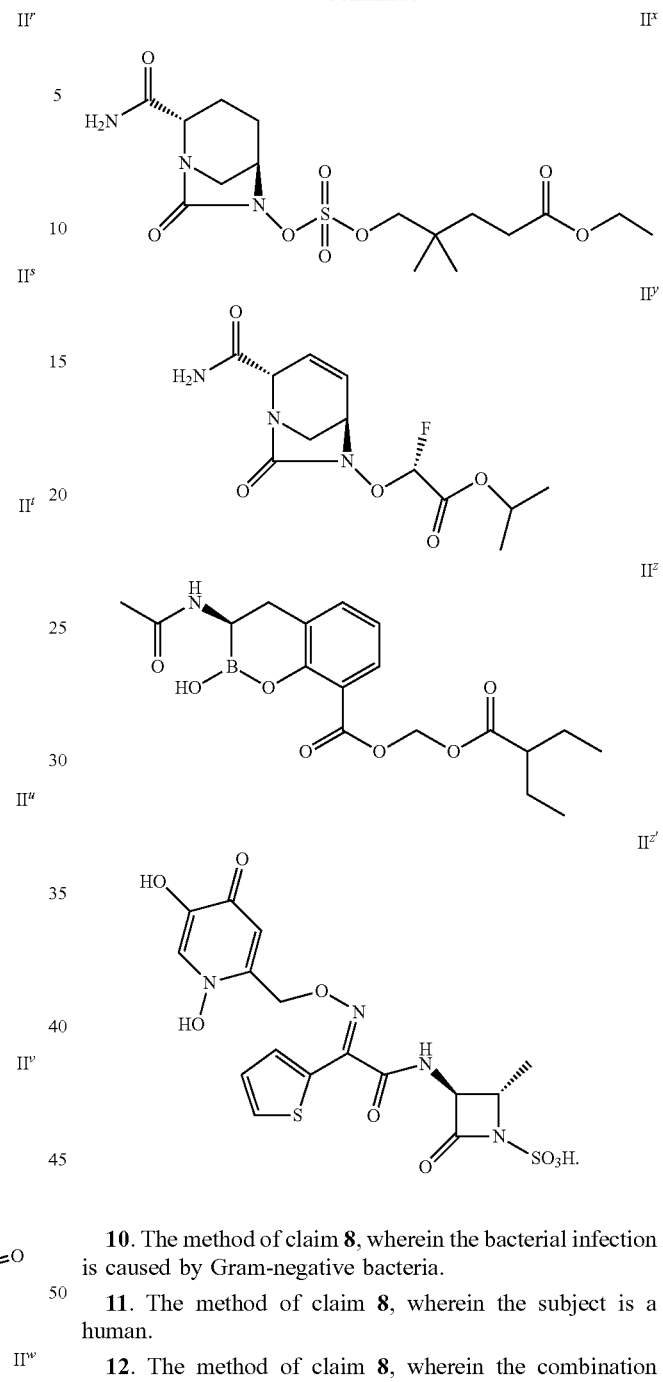

10. The method of claim 8, wherein the bacterial infection is caused by Gram-negative bacteria.

11. The method of claim 8, wherein the subject is a human.

12. The method of claim 8, wherein the combination comprises a ratio of LTV-17 (I) to β-lactamase inhibitor in a range of 20:1 to 1:20, by weight.

13. The method of claim 12, wherein the ratio is in the range of 1:1 to 1:20.

14. The method of claim 8, wherein the pharmaceutical combination further comprises a pharmaceutically acceptable diluent, excipient or carrier.

* * * * *